United States Patent
Iwai et al.

(10) Patent No.: US 11,714,086 B2
(45) Date of Patent: Aug. 1, 2023

(54) IMMUNE FUNCTION EVALUATION METHOD AND ELISA SYSTEM THEREFOR

(71) Applicants: UNIVERSITY OF OCCUPATIONAL AND ENVIRONMENTAL HEALTH, JAPAN, Kitakyushu (JP); NIPPON MEDICAL SCHOOL FOUNDATION, Tokyo (JP)

(72) Inventors: Yoshiko Iwai, Tokyo (JP); Masahiro Takeuchi, Kitakyushu (JP); Tomomitsu Doi, Kitakyushu (JP)

(73) Assignees: UNIVERSITY OF OCCUPATIONAL AND ENVIRONMENTAL HEALTH, JAPAN, Kitakyushu (JP); NIPPON MEDICAL SCHOOL FOUNDATION, Tokyo (JP)

( * ) Notice: Subject to any disclaimer, the term of this patent is extended or adjusted under 35 U.S.C. 154(b) by 580 days.

(21) Appl. No.: 16/645,225

(22) PCT Filed: Sep. 7, 2018

(86) PCT No.: PCT/JP2018/033161
§ 371 (c)(1),
(2) Date: Mar. 6, 2020

(87) PCT Pub. No.: WO2019/049974
PCT Pub. Date: Mar. 14, 2019

(65) Prior Publication Data
US 2020/0284792 A1    Sep. 10, 2020

(30) Foreign Application Priority Data
Sep. 8, 2017  (JP) ................. 2017-172593

(51) Int. Cl.
*G01N 33/569* (2006.01)
*G01N 33/543* (2006.01)

(52) U.S. Cl.
CPC . *G01N 33/56972* (2013.01); *G01N 33/54306* (2013.01); *G01N 2800/52* (2013.01)

(58) Field of Classification Search
None
See application file for complete search history.

(56) References Cited

U.S. PATENT DOCUMENTS 5,629,204 A    5/1997   Honjo et al.
5,698,520 A   12/1997   Honjo et al.

FOREIGN PATENT DOCUMENTS

JP    H05-336973 A    12/1993
JP    H07-291996 A    11/1995

OTHER PUBLICATIONS

Li-Hui et el. Chinese Journal of Biotechnology, vol. 23, issue 1, Jan. 2007 (Year: 2007).*
Takeuchi et al. Immunology Letters 196, pp. 155-160, Jan. 2018 (Year: 2018).*
Li_Hui et al, Chinese Journal of Biotechnology, vol. 23. Issue 1, pp. 106-111, Jan. 2007. (Year: 2007).*
Brahmer et al., "Nivolumab versus Docetaxel in Advanced Squamous-Cell Non-Small-Cell Lung Cancer," *N. Engl. J. Med.*, 373(2): 123-135 (2015).
Chen et al., "Development of a sandwich ELISA for evaluating soluble PD-L1 (CD274) in human sera of different ages as well as supernatants of PD-L1+ cell lines," *Cytokine*, 56(2): 231-238 (2011).
Garon et al., "Pembrolizumab for the Treatment of Non-Small-Cell Lung Cancer," *N. Engl. J. Med.*, 372(21): 2018-2028 (2015).
Herbst et al., "Predictive correlates of response to the anti-PD-L1 antibody MPDL3280A in cancer patients," *Nature*, 27: 515(7528): 563-567 (2014).
Li et al., "Glycosylation and stabilization of programmed death ligand-1 suppresses T-cell activity," *Nat. Commun.*, 7: 12632 (2016).
Smithy, "Predicting Response to Anti-Pd-1 Immunotherapy in Metastatic Melanoma," *Yale Medicine Thesis Digital Library*, Thesis No. 2172: 1-74 (2017).
Takeuchi et al., "Soluble PD-L1 with PD-1 binding capacity exists in the plasma of patients with non-small cell lung cancer," *Immunol. Lett.*, 196: 155-160 (2018).
Xu et al., "Preparation and Identification of Human Soluble sPD-LI and Its Antibodies," *Chin. J. Biotech.*, 23(1): 106-111 (2007).
Zhang et al., "Circulating PD-L1 in NSCLC patients and the correlation between the level of PD-L1 expression and the clinical characteristics," *Thorac. Cancer*, 6(4): 534-538 (2015).
Zhao et al., "Plasma levels of soluble programmed death ligand-1 may be associated with overall survival in nonsmall cell lung cancer patients receiving thoracic radiotherapy," *Medicine*, 96(7): e6102 (2017).
Japanese Patent Office, International Search Report in International Patent Application No. PCT/JP2018/033161 (dated Dec. 11, 2018).
Japanese Patent Office, International Preliminary Report on Patentability in International Patent Application No. PCT/JP2018/033161 (dated Mar. 10, 2020).

* cited by examiner

*Primary Examiner* — Jana A Hines
*Assistant Examiner* — Khatol S Shahnan Shah
(74) *Attorney, Agent, or Firm* — Leydig, Voit & Mayer, Ltd.

(57) ABSTRACT

The present invention aims to develop a method capable of evaluating T cell immune function. A method for evaluating T cell immune function including detecting and quantifying soluble PD-L1 having a binding ability to PD-1, and an ELISA system used for detecting and quantifying bsPD-L1, including a carrier with a solid-phased PD-1 protein, a means for reacting the carrier and a test sample, and a means for detecting and quantifying soluble PD-L1 bound to the carrier as bsPD-L1.

7 Claims, 6 Drawing Sheets

IMMUNE FUNCTION EVALUATION METHOD AND ELISA SYSTEM THEREFOR

CROSS-REFERENCE TO RELATED APPLICATIONS

This patent application is the U.S. national phase of International Patent Application No. PCT/JP2018/033161, filed Sep. 7, 2018, which claims the benefit of Japanese Patent Application No. 2017-172593, filed on Sep. 8, 2017, which are incorporated by reference in their entireties herein.

TECHNICAL FIELD

The present invention relates to a method for evaluating immunity of an individual, particularly T cell immune function. More particularly, the present invention relates to an evaluation method for evaluating T cell immune function by detecting and quantifying soluble PD-L1 having a PD-1 binding ability in a sample of biological origin, such as blood and the like, and a novel ELISA system based on a binding reaction with PD-1 as a measurement principle.

BACKGROUND ART

Diseases in which T cell immunity is involved in the pathology include not only cancer but also various diseases such as infectious diseases, autoimmune diseases, allergies, rejection in transplantation, and lifestyle-related diseases.

As the situation stands, there are almost no means to evaluate immune function of an individual, particularly T cell function, in clinical practice. At present, immunity-related indices in blood tests that are routinely performed in clinical practice include leukocyte count, leukocyte fraction, immunoglobulin, CRP and the like. These test items cannot evaluate T cell function of an individual. As a molecule that controls T cell function, PD-1/PD-L1 is known.

PD-1 is a membrane protein expressed on the surface of T cell and the like (patent documents 1, 2). PD-L1 and PD-L2 have been identified as ligands for PD-1, and it is known that these molecules bind to PD-1 and suppress T cell function, whereby immunity is suppressively regulated.

It is also known that cancer and virus-infected cells escape immune surveillance of the host by expressing PD-1 ligand and binding to PD-1.

Among these ligands of PD-1, PD-L1 includes a membrane type expressed on the cell surface and a soluble type present in blood.

It is known that membrane-type PD-L1 is stabilized by N-glycosylation, which inhibits degradation and increases binding ability to PD-1 (non-patent document 1). On the other hand, soluble PD-L1 is known to be glycosylated but its significance has not been clarified.

A medicament developed focusing on this PD-1/PD-L1 signal is, for example, an anti-PD-1 antibody, Nivolumab preparation (product name: OPDIVO).

Nivolumab releases the brakes on the immune system by inhibiting an immune checkpoint molecule, PD-1, enhances immune responses to cancer and exhibits antitumor effects. The efficiency rate of Nivolumab is generally 20 to 30%, and patients are divided into a high sensitive group and a low sensitive group.

Various attempts have been made to predict the drug sensitivity thereof, and one of them is an attempt to determine whether or not it is applicable by examining the expression of PD-L1 in tumor tissues.

In addition, using blood samples from patients before and after an anti-PD-1 antibody treatment, whether soluble PD-L1 in the blood could be a biomarker to determine therapeutic effects of anti-PD-1 antibody treatments has been studied. Also, the relationship between soluble PD-L1 and prognosis has been investigated. For example, in a test targeting 109 non-small cell lung cancer patients, an inverse correlation between the expression of soluble PD-L1 and prognosis (poor prognosis in high soluble PD-L1 level group compared with low level group) has been reported, like PD-L1 in tissues (non-patent document 2).

However, no consensus has been obtained at present on the relationship between PD-L1 expression in tissues, and the prognosis of cancer or the efficiency rate of immune checkpoint inhibitors (non-patent documents 3 to 5). Additionally, there is a problem in immunohistological examination that quantification and standardization are difficult to perform because of influence of biopsy sampling sites and variation among test laboratories.

DOCUMENT LIST

Patent Documents patent document 1: JP-A-H5-336973
patent document 2: JP-A-H7-291996

Non-Patent Documents non-patent document 1: Li C W et al. Nat Commun. 2016 Aug. 30; 7:12632.
non-patent document 2: Zhang J et al. Thorac Cancer. 2015 July; 6(4):534-8
non-patent document 3: Brahmer J et al. N Engl J Med. 2015 Jul. 9; 373(2):123-35.
non-patent document 4: Garon E B et al. N Engl J Med. 2015 May 21; 372(21):2018-28.
non-patent document 5: Herbst R S et al. Nature. 2014 Nov. 27; 515(7528):563-7.

SUMMARY OF THE INVENTION

Problems to be Solved by the Invention

In view of the above-mentioned circumstances, a first problem of the present invention is to develop a method capable of evaluating T cell immune function of an individual. A second problem is to develop a diagnostic marker that permits evaluation of the pathology and determination of the therapeutic effect of a disease involving T cell immunity. Furthermore, a third problem is to develop a method enabling prediction of the prognosis of cancer, diagnosis of applicability of immunotherapy with an immune checkpoint inhibitor and the like, and prediction of therapeutic effects and side effects.

Means of Solving the Problems

The present inventors took note of soluble PD-L1 (hereinafter "sPD-L1") in blood as being capable of evaluating a systemic immune function and started the research. The present inventors have clarified that sPD-L1 includes binding type soluble PD-L1 (PD-1 binding sPD-L1, hereinafter "bsPD-L1") having a high binding ability to PD-1. In addition, they have clarified that a similar mechanism exists in PD-L1 expressed on a membrane surface.

bsPD-L1 is subject to various sugar chain modifications as one embodiment, the binding ability to PD-1 changes depending on the site and degree thereof, and the PD-1 binding ability becomes low by deglycosylation. The inventors have clarified the importance of sugar chain modification of sPD-L1 in PD-1 binding. In addition, they have clarified that true evaluation of bsPD-L1 requires detection and quantification using the PD-1 protein itself as an antigen.

As a result, the inventors have completed the invention relating to an evaluation method including detection and quantification of a binding reaction of PD-1 and bsPD-L1.

Conventionally, as a method for detecting and quantifying sPD-L1, there is a method for detecting and quantifying sPD-L1 by ELISA using an anti-PD-L1 antibody immobilized on a microplate. However, the inventors confirmed that the conventional method cannot appropriately quantify or evaluate bsPD-L1 having a high binding ability to PD-1 even though it can quantify sPD-L1.

Based on the above findings, the present inventors produced an ELISA plate that can more appropriately detect and quantify bsPD-L1 by immobilizing the PD-1 protein itself on a microplate and completed the invention.

The present invention has the following constitution.

(1) A method for evaluating T cell immune function, comprising a step of reacting a test sample and PD-1, and a step of detecting and quantifying a soluble PD-L1 bound to PD-1 as "soluble PD-L1 having a PD-1 binding ability (bsPD-L1)".

(2) The evaluation method of the above-mentioned (1), wherein the bsPD-L1 is a sugar chain-modified PD-L1.

(3) The evaluation method of the above-mentioned (1) or (2), wherein the test sample is a sample of biological origin.

(4) The evaluation method of any of the above-mentioned (1) to (3), further comprising a step of reacting an anti-PD-L1 antibody and the aforementioned test sample, and detecting and quantifying soluble PD-L1 (sPD-L1) in the test sample, wherein the results are combined and evaluated.

(5) The evaluation method of any of the above-mentioned (1) to (4), further comprising a step of evaluating pathology, prognosis or treatment effect in a disease involving T cell immunity, or a step of aiding the evaluation.

(6) The evaluation method of the above-mentioned (5), wherein the disease involving T cell immunity is cancer.

(7) The evaluation method of any of the above-mentioned (1) to (4), further comprising a step of evaluating diagnosis of applicability, treatment effect and side effect prediction of immunotherapy, or a step of aiding the evaluation.

(8) The evaluation method of the above-mentioned (6), wherein a good prognosis can be predicted when the amount or concentration of bsPD-L1 in the test sample is not less than the cutoff value.

(9) A biomarker for evaluation of T cell immune function which comprises bsPD-L1.

(10) A combination of biomarkers for evaluation of T cell immune function, comprising bsPD-L1 and sPD-L1.

(11) The biomarker of the above-mentioned (9) or the combination of the biomarkers of the above-mentioned (10), wherein the T cell immune function evaluation is for evaluating pathology, prognosis or treatment effect in a disease involving T cell immunity.

(12) The biomarker of the above-mentioned (9) or the combination of the biomarker of the above-mentioned (10), wherein the T cell immune function evaluation is for evaluating diagnosis of applicability, treatment effect or side effect prediction of immunotherapy.

(13) A system for detecting and quantifying bsPD-L1 in a test sample, comprising a PD-1 protein, a means for reacting the protein and a test sample, and a means for detecting and quantifying soluble PD-L1 bound to the protein as bsPD-L1.

(14) The system of the above-mentioned (13), further comprising an anti-PD-L1 antibody, a means for reacting the antibody and a test sample, and a means for detecting and quantifying soluble PD-L1 bound to the antibody.

(15) The system of the above-mentioned (13) or (14), wherein the system is an ELISA system.

(16) The system of any of the above-mentioned (13) to (15) for evaluating pathology, prognosis or treatment effect in a disease involving T cell immunity, or aiding the evaluation.

(17) The system of any of the above-mentioned (13) to (15) for evaluating diagnosis of applicability, prognosis, treatment effect and side effect prediction of immunotherapy, or aiding the evaluation.

(18) An ELISA kit comprising a carrier with a PD-1 protein solid-phased thereon and a detection marker for detecting soluble PD-L1 bound to the carrier as bsPD-L1, and optionally comprising a carrier with an anti-PD-L1 antibody solid-phased thereon and a detection marker for detecting soluble PD-L1 bound to the carrier as sPD-L1.

(19) A method for evaluating pathology, prognosis or treatment effect in a disease involving T cell immunity, or aiding the evaluation, which comprises a step of deglycosylating soluble PD-L1 in a sample of biological origin, and a step of analyzing the pattern of deglycosylation of the soluble PD-L1 obtained in the step.

(20) A method for evaluating diagnosis of applicability, treatment effect and side effect prediction of immunotherapy, or aiding the evaluation, which comprises a step of deglycosylating soluble PD-L1 in a sample of biological origin, and a step of analyzing the pattern of deglycosylation of the soluble PD-L1 obtained in the step.

Another constitution of the present invention is as follows.

A first constitution of the present invention is a method for evaluating T cell immune function, comprising detecting and quantifying soluble PD-L1 having binding ability to PD-1 (hereinafter "bsPD-L1").

A second constitution of the present invention is the evaluation method described in the first constitution, wherein the bsPD-L1 is a sugar chain-modified PD-L1.

A third constitution of the present invention is the evaluation method described in the first or second constitution, wherein the bsPD-L1 is bsPD-L1 contained in a sample of biological origin.

A fourth constitution of the present invention is the evaluation method described in any of the first to the third constitutions, wherein the sample of biological origin is one or more kinds selected from blood, lung lavage fluid, urine, and cerebrospinal fluid.

A fifth constitution of the present invention is the evaluation method described in any of the first to the fourth constitutions, wherein the sample of biological origin is derived from a mammal.

A sixth constitution of the present invention is the evaluation method described in any of the first to the fifth constitutions for evaluating pathology and treatment effect in a disease involving T cell immunity.

A seventh constitution of the present invention is the evaluation method described in any of the first to the fifth constitutions for evaluating diagnosis of applicability, treatment effect and side effect prediction of immunotherapy including immunity check point inhibitor.

An eighth constitution of the present invention is the evaluation method described in the sixth or the seventh constitution, wherein the disease is cancer, infectious disease, autoimmune disease, allergy, rejection in transplantation, or lifestyle-related disease.

A ninth constitution of the present invention is the evaluation method described in the eighth constitution, wherein the cancer is any of carcinoma, squamous cell carcinoma (cervix, eyelids, conjunctiva, vagina, lung, mouth cavity, skin, bladder, tongue, larynx, esophagus), or glandular cancer (prostate, small intestine, endometrium, cervix, large intestine, lung, pancreas, esophagus, rectal, uterus, stomach, breast, ovary), sarcoma (myogenic sarcoma), leukemia, neuroma, melanoma, and lymphoma.

A tenth constitution of the present invention is the evaluation method described in the eighth constitution, wherein the infectious disease is with any of human hepatitis virus (hepatitis B, hepatitis C, hepatitis A or hepatitis E), human retrovirus, human immunodeficient virus (HIV1, HIV2), human T cell leukemia virus, and human T-lymphtropic virus (HTLV1, HTLV2).

An eleventh constitution of the present invention is the evaluation method described in the eighth constitution, wherein the autoimmune disease is type 1 diabetes, systemic lupus erythematosus, rheumatoid arthritis, ulcerative colitis, Crohn's disease, multiple sclerosis, scleroderma, vulgaris pemphigus, psoriasis, atopic dermatitis, Celiac disease, Hashimoto's thyroiditis, Graves' disease (thyroid gland), Sjogren's syndrome, Guillain-Barre syndrome, Goodpasture's syndrome, Addison's disease, Wegener's granulomatosis, primary biliary sclerosis, sclerosing cholangitis, autoimmune hepatitis, rheumatic polymyalgia, Raynaud's phenomenon, temporal arteritis, giant cell arteritis, autoimmune hemolytic anemia, malignant anemia, polyarteritis *nodosa*, Behcet's disease, primary biliary cirrhosis, uveitis, myocarditis, rheumatic fever, ankylopoietic spondylarthritis, glomerulonephritis, sarcoidosis, dermatomyositis, myasthenia gravis, or polymyositis.

A twelfth constitution of the present invention is the evaluation method described in any of the fourth to the eleventh constitutions, further comprising reacting an anti-PD-L1 antibody and the aforementioned test sample of biological origin, and evaluating the results of detection and quantification of PD-L1 in combination.

A thirteenth constitution of the present invention is an ELISA system used for detection and quantification of bsPD-L1, which is composed of a carrier with a solid-phased PD-1 protein, wherein the carrier is reacted with a sample of biological origin containing bsPD-L1, and a detection marker in this order.

A fourteenth constitution of the present invention is the ELISA system described in the thirteenth constitution, wherein the carrier is composed of at least one kind selected from a microplate, a bead and a tube.

A fifteenth constitution of the present invention is the ELISA system described in the thirteenth or the fourteenth constitution, wherein the aforementioned detection marker is composed of at least one kind selected from an enzyme-labeled antibody, a fluorescence-labeled form, and a radio-labeled form.

A sixteenth constitution of the present invention is the ELISA system described in any of the thirteenth to the fifteenth constitution, wherein the carrier with the solid-phased anti-PD-L1 antibody is reacted with a sample of biological origin containing bsPD-L1, and a detection marker in this order, and the results of detection and quantification are evaluated in combination.

A seventeenth constitution of the present invention is an ELISA kit comprising the ELISA system described in any of the thirteenth to the sixteenth constitutions, an anti-PD-L1 antibody, and a detection marker.

Effect of the Invention

According to the present invention, a method capable of evaluating T cell immune function can be provided.

That is, the inventors have found in the present invention that the PD-1 binding property of soluble PD-L1 mainly depends on the modification of sugar chain. Using this as a measurement principle, a new evaluation method for detecting and quantifying soluble PD-L1 having a PD-1 binding ability can be provided.

Furthermore, as one specific embodiment of this evaluation method, an ELISA system has been completed by the inventors, by which influence of biopsy sites and variation among test laboratories are reduced compared to immunohistological examination, the quantification of T cell immune function is facilitated, and the T-cell immune function can be evaluated systemically, not topically.

According to these inventions, provision of diagnoses of pathology of various diseases involving T cell immune response, prognosis of cancer, applicability of immunotherapy including immune checkpoint inhibitors and treatment effects, and an aiding means for the diagnosis can be expected.

DESCRIPTION OF EMBODIMENTS

Figure 1:
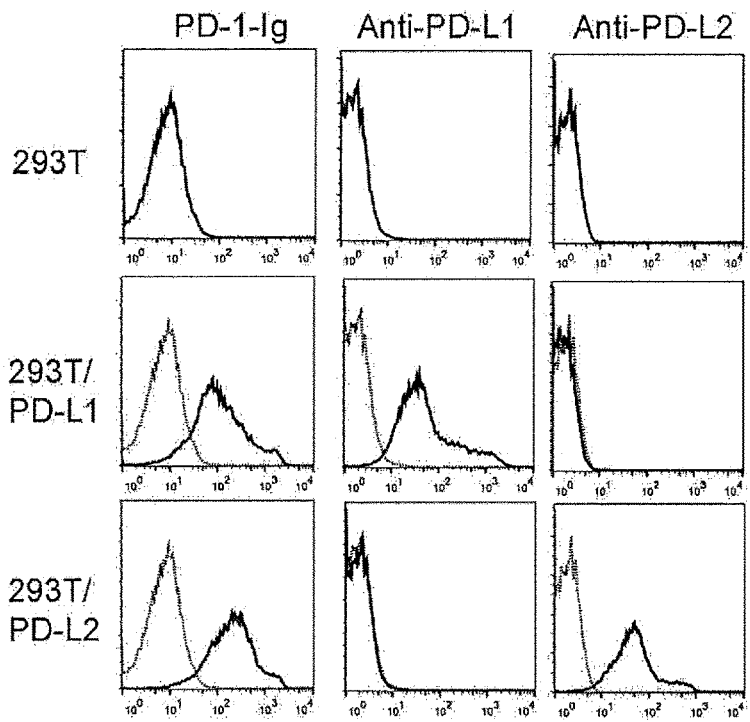
FIG. 1 shows the results of FACS analysis confirming reaction of the produced anti-PD-1 antibody (PD-1-Ig) protein with each ligand.

A method for evaluating immune function, specifically T cell immune function and the like, of the present invention is explained.

The method for evaluating T cell immune function of the present invention is characterized by detecting and quantifying soluble PD-L1 having a binding ability to PD-1 (hereinafter to be also referred to as "bsPD-L1").

As shown in the below-mentioned Examples, the inventors have found that the PD-1 binding property of soluble PD-L1 is mainly dependent on the sugar chain modification, and the evaluation method of the present invention is based thereon as the measurement principle.

Soluble PD-L1 in blood (hereinafter to be also referred to as "sPD-L1") includes binding type soluble PD-L1 having a high binding ability to PD-1 (same as bsPD-L1), and a similar mechanism also exists in PD-L1 expressed on a membrane surface.

In one embodiment, bsPD-L1 undergoes various sugar chain modifications, the binding ability to PD-1 varies depending on the site and degree thereof, and deglycosylation lowers the PD-1 binding ability.

One preferable embodiment of the evaluation method of the present invention includes a step of reacting a test sample and PD-1, and a step of detecting and quantifying soluble PD-L1 bound to PD-1 (i.e., PD-L1 having PD-1 binding ability: bsPD-L1).

In the present invention, PD-1 is defined as a protein called Programmed cell death protein 1, and plays a role of an antigen (receptor) for detecting bsPD-L1. PD-1 does not need to be particularly limited as long as it plays this role, and various types can be used.

That is, depending on the subject to be evaluated, PD-1 derived from the corresponding species, such as human, mouse, rat, rabbit, horse, etc., may be used, and one derived from mammals can be preferably used. Among them, for example, in the case of human, a protein consisting of 288 amino acid residues specified by Q15116 in UniProtKB Accession may be used.

It is not intended to exclude any modification of PD-1 of the present invention. That is, as long as the binding of bsPD-L1 and PD-1, which is the principle of the present invention, can be achieved, alteration and modification of PD-1 suitable for each evaluation system may be performed.

As PD-1, one artificially produced is preferable, but limitation to this is not intended and one with a biological origin may also be used.

When artificially producing PD-1, it can be produced by a known method. That is, PD-1 can be produced by introducing a PD-1 expression vector into a cell, and culturing and purifying same (see Outline of experiment method, 2 to 4).

Alternatively, PD-1 may be separated from a sample of biological origin, and used. The purified bsPD-L1 may also be reacted with a sample of biological origin, such as a cancer section etc., and evaluated by immunostaining or the like.

In the present invention, bsPD-L1 is defined as soluble PD-L1 having a high binding ability to PD-1.

One embodiment of bsPD-L1 includes sugar chain-modified soluble PD-L1. The binding property of soluble PD-L1 to PD-1 depends on the sugar chain modification, and T cell immune function can be evaluated by detection and quantification of sugar chain-modified PD-L1.

Furthermore, the degree and site of the sugar chain modification of bsPD-L1 do not need to be particularly limited as long as it has a high binding ability to PD-1. One example of bsPD-L1 is one containing a sugar chain and having a molecular weight of about 45 to 65 Kd.

In the evaluation method of the present invention, the test sample is preferably a sample of biological origin. By detecting and quantifying bsPD-L1 in a sample of biological origin in an individual, the T cell immune function of the individual can be evaluated.

In this case, the sample of biological origin only needs to have a possibility that bsPD-L1 may be present, and it does not matter even if bsPD-L1 eventually does not exist.

The sample of biological origin does not need to be particularly limited as long as it is derived from a living organism, and various samples of biological origin can be used.

As such sample of biological origin, a sample directly collected from a living body, a sample obtained by washing or disrupting the sample, and the like can be used. Examples thereof include blood, a washing solution of tissue such as alveoli and the like, urine, cerebrospinal fluid, tissue section and the like. These samples of biological origin can be used as they are depending on the evaluation system, or may be used as test samples after a certain pretreatment.

As a sample of biological origin, blood, a washing solution of tissue such as alveoli and the like, urine, or cerebrospinal fluid is preferably used.

This makes it possible to perform measurement by ELISA and the like rather than immunohistological examination, and provides the effects of eliminating influence of biopsy sites and variation among test laboratories, and facilitating the quantification of T cell immune function. Furthermore, the present invention provides an effect that the T-cell immune function can be evaluated systemically, not topically.

In the present invention, the evaluation of immune function is defined in a broad sense as evaluation of the function of the entire immune system controlling an individual, and is defined in a narrow sense as evaluation of the T cell immune function.

In addition, T cell immune function evaluation is defined as evaluation of any state involving T cell immunity, and includes, for example, evaluation of T cell immune state in an individual.

It is preferable to use the T cell immune function evaluation for evaluating pathology, prognosis or treatment effect in a disease involving T cell immunity. This makes it possible to predict the disease state (diagnosis of disease stage), the speed and degree of recovery (prognosis prediction), the effect of the medicament, and the like through the evaluation of the T cell immune function, and provides an effect of improving the usefulness of the present invention.

The disease does not need to be particularly limited as long as it is a disease involving T cells, and includes, for example, cancer, infectious disease, autoimmune disease, allergy, rejection in transplantation, lifestyle-related disease and the like.

In addition, as an effect prediction of a medicament used for a disease, use for predicting the effect of a medicament whose efficacy pharmacology is PD-1/PD-L1 signaling inhibition is expected, and more preferably, use for predicting the effect of a medicament containing an anti-PD-1 antibody such as OPDIVO as an active ingredient is expected.

As shown in the below-mentioned Examples, the amount or concentration of bsPD-L1 in a biological sample derived from a cancer patient is correlated with the prognosis of the patient, and the prognosis is predicted to be good when the amount or concentration of bsPD-L1 is not less than the cutoff value, as determined by the evaluation method of the present invention. The cutoff value is also referred to as a pathology identification value, and is a value set for the purpose of diagnosing a disease or a pathology. The cut-off value varies depending on the kind of a sample of biological origin (e.g., serum or plasma), the presence or absence and the kind of coagulant when the biological sample is blood, the processing method from blood collection to storage (temperature and time), storage conditions (storage temperature and storage period), and an optimum value can be set as appropriate. It is desirable to set the optimum value in advance from the viewpoint of accuracy. In a preferable embodiment, the prognosis after cancer treatment is evaluated based on whether the amount or concentration of bsPD-L1 is not less than the cutoff value. When it is not less than the cutoff value, the prognosis is considered to be good.

Among the diseases, examples of the cancer include carcinoma, squamous cell carcinoma (cervix, eyelids, conjunctiva, vagina, lung, mouth cavity, skin, bladder, tongue, larynx, esophagus cancers), and glandular cancer (prostate, small intestine, endometrium, cervix, large intestine, lung, pancreas, esophagus, rectal, uterus, stomach, breast, ovary cancers). It further includes sarcoma (e.g., myogenic sarcoma), leukemia, neuroma, melanoma, and lymphoma.

Examples of the infectious disease include infection with human hepatitis (hepatitis B, hepatitis C, hepatitis A or hepatitis E) virus, human retrovirus, human immunodeficiency virus (HIV1, HIV2), human T cell leukemia virus, human T-lymphtropic virus (HTLV1, HTLV2). Examples of other infectious disease include infection with simple herpes virus type 1 and type 2, Epstein Barr virus, cytomegalovirus, varicella-herpes zoster virus, human herpes virus including human herpes virus 6, polio virus, measles virus, rubella virus, Japanese encephalitis virus, mumps virus, influenza virus, adenovirus, enterovirus, rhino virus, virus developing severe acute respiratory syndrome (SARS), Ebola virus, West Nile virus and the like.

Examples of the autoimmune disease include type 1 diabetes, systemic lupus erythematosus, rheumatoid arthritis, ulcerative colitis, Crohn's disease, multiple sclerosis, scleroderma, vulgaris pemphigus, psoriasis, atopic dermatitis, Celiac disease, Hashimoto's thyroiditis, Graves' disease (thyroid gland), Sjogren's syndrome, Guillain-Barre syndrome, Goodpasture's syndrome, Addison's disease, Wegener's granulomatosis, primary biliary sclerosis, sclerosing cholangitis, autoimmune hepatitis, rheumatic polymyalgia, Raynaud's phenomenon, temporal arteritis, giant cell arteritis, autoimmune hemolytic anemia, malignant anemia, polyarteritis *nodosa*, Behcet's disease, primary biliary cirrhosis, uveitis, myocarditis, rheumatic fever, ankylopoietic spondylarthritis, glomerulonephritis, sarcoidosis, dermatomyositis, myasthenia gravis, polymyositis and the like.

In the evaluation method of the present invention, the evaluation is preferably performed in combination with a conventional method. That is, a test sample (preferably, a sample of biological origin) is reacted with an anti-PD-L1 antibody as an antigen, sPD-L1 is detected and quantified, and the results are combined and evaluated, whereby the difference between sPD-L1 and bsPD-L1, namely, the state of sugar chain modification in soluble PD-L1 can be estimated, and more appropriate evaluation of T cell immune function and elucidation of the pathology can be expected.

The evaluation method of the present invention does not need to be particularly limited as long as the binding reaction between PD-1 and bsPD-L1 can be detected and quantified, and can be performed in various constitutions or embodiments. As an embodiment of the evaluation method of the present invention, for example, a measurement device and a measurement instrument, a preliminary element and an element set therefor, and the like can be mentioned.

A preferable embodiment of the present invention is, for example, a system for detecting and quantifying bsPD-L1 in a test sample, including a PD-1 protein, a means for reacting the protein and a test sample, and a means for detecting and quantifying soluble PD-L1 bound to the protein as bsPD-L1. Preferably, it further includes an anti-PD-L1 antibody, a means for reacting the antibody and a test sample, and a means for detecting and quantifying soluble PD-L1 bound to the antibody.

Among the above-mentioned systems, the most preferred embodiment of the present invention is a novel ELISA system. In the present embodiment, the binding reaction between the PD-1 protein and bsPD-L1 is performed on a carrier on which the PD-1 protein is immobilized, that is, the principle of the ELISA method is used. As the carrier, those similar to the carrier used in the ELISA system of the present invention described later can be used. As the specific procedures of the step of contacting the carrier and the test sample, and the step of detecting and quantifying bsPD-L1 in the test sample, and the materials and apparatuses in the steps, procedures, materials and apparatuses similar to those of the ELISA system of the present invention described later can be utilized. This provides effects that influence of biopsy sites and variation among test laboratories are less compared to immunohistological examination, the quantification of T cell immune function is facilitated, and the T-cell immune function can be evaluated systemically, not topically.

The ELISA system of the present invention (sometimes to be referred to as "new ELISA system") is a system including a carrier with a solid-phased PD-1 protein (hereinafter to be also referred to as "PD-1 carrier"), a means for reacting the carrier and a test sample (preferably, a sample of biological origin), and a means for detecting and quantifying soluble PD-L1 bound to the carrier as bsPD-L1. Preferably, it further includes a carrier with a solid-phased anti-PD-L1 antibody (hereinafter to be also referred to as "anti-PD-L1 antibody carrier"), a means for reacting the carrier and the aforementioned test sample and a means for detecting and quantifying soluble PD-L1 bound to the carrier.

The carrier plays a role of a carrier for solid-phasing the PD-1 protein. The carrier does not need to be particularly limited as long as it plays this role, and those of various materials and shapes can be used. As the carrier, a microplate, a bead, a tube, and the like made of a hydrophobic plastic material can be typically used, and most preferably, a multi-well microplate can be used.

The PD-1 carrier can be produced by a known method. That is, a solution in which PD-1 protein is dissolved is added to the carrier and allowed to stand. After adsorption of the PD-1 protein to the carrier, the solution is removed, and washing or protection with a blocking solution and washing is performed, whereby PD-1 carrier can be produced (see Experimental Example 2).

In the new ELISA system of the present invention, a test sample (preferably, a sample of biological origin) and a detection marker are sequentially reacted with the carrier.

A test sample to be reacted with the prepared PD-1 carrier is, for example, a sample of biological origin as described in the evaluation method of the present invention, and does not need to be particularly limited as long as the binding between PD-1 and bsPD-L1 on the PD-1 carrier is achieved. It may be used as it is or after a pretreatment according to the PD-1 carrier. For example, in the case of blood, a plasma component can be obtained by centrifugation, and it is diluted where necessary and can be used as a test sample.

Also, when the reaction between the PD-1 carrier and the test sample is performed, the reaction time and reaction temperature can be adjusted according to the PD-1 carrier and the test sample to be used. After the reaction, the supernatant may be removed and washing may be performed with a washing liquid as necessary.

After completion of the reaction with the test sample, a detection marker is reacted.

The detection marker serves as a marker for detecting the binding reaction between PD-1 and bsPD-L1, and enables detection and quantification of the binding reaction through detection of the detection marker. The detection marker does not need to be particularly limited as long as it plays these roles, and can be performed in various embodiments.

The detection marker can be constituted, for example, as a marker for directly or indirectly detecting bsPD-L1 bound to PD-1.

Direct detection includes, for example, reacting a radiolabeled or fluorescence-labeled anti-PD-L1 antibody as a detection marker with bsPD-L1 bound to PD-1.

Indirect detection includes, for example, reacting a biotin-labeled anti-PD-L1 antibody with bsPD-L1 bound to PD-1, followed by detection by reacting with a biotin quantification reagent as a detection marker.

The detection marker does not need to be particularly limited as long as detection is possible, and can be appropriately changed depending on the embodiment of the PD-1 carrier and the purpose of measurement. For example, an enzyme-labeled antibody, a fluorescence-labeled form, a radiolabeled form, or a combination of these can be used.

The ELISA system of the present invention is preferably an ELISA system that further reacts a carrier with solid-phased anti-PD-L1 antibody (hereinafter to be referred to as "anti-PD-L1 antibody carrier") with a test sample containing bsPD-L1 (preferably, a sample of biological origin) and a detection marker in this order, combines the detection and quantification results, and performs evaluation. The ELISA system includes a new ELISA system containing the above-mentioned PD-1 carrier and having a means for sequentially reacting a test sample and a detection marker, and additionally contains an anti-PD-L1 antibody carrier, and has a means for sequentially reacting a test sample and a detection marker with the carrier. As a result, simultaneous detection and quantification of sPD-L1 and bsPD-L1 can be performed, which affords an effect that a more appropriate evaluation of T cell immune function can be performed.

In such a case, a particular limitation is not necessary as long as simultaneous detection and quantification of PD-L1 and bsPD-L1 is possible, and various embodiments and constitutions may be employed.

For example, a half of a 96-well microplate is solid-phased with PD-1 protein, and the rest is solid-phased with anti-PD-L1 antibody. In addition, an ELISA kit containing a PD-1 carrier, an anti-PD-L1 antibody carrier, and an anti-PD-L1 antibody as a detection marker may be constituted.

Since simultaneous detection and quantification of sPD-L1 and bsPD-L1 is possible, the ratio of bsPD-L1 in sPD-L1 can be calculated. By correlating the ratio and applicability of various treatments such as immunotherapy and the like, the presence or absence of a treatment effect, the presence or absence of side effects, and the like, the ratio can be used as an index for diagnosis of applicability of various treatments (e.g., immunotherapy), and prediction of a therapeutic effect and side effects.

Therefore, in the present invention, bsPD-L1 can be a biomarker for evaluating T cell immune function. A biomarker is a substance in a living body such as a protein, a gene and the like contained in a body fluid or tissue such as blood, urine and the like, which correlates with a change in a disease or a response to a treatment and becomes an index. By measuring the amount of the biomarker, one of the indices of the presence and progress of a disease and the effect of a treatment can be provided. bsPD-L1 can be used as an index in evaluation of the pathology, prognosis or treatment effect in diseases involving T cell immunity. Use in combination with sPD-L1 enables more detailed evaluation. Therefore, the present invention also provides a combination of biomarkers for evaluating T cell immune function, which is composed of a biomarker consisting of bsPD-L1 and a biomarker consisting of sPD-L1.

The ELISA system of the present invention is preferably constituted as an ELISA kit. This provides an effect that quick, simple, and highly reproducible evaluation of T cell immune function is possible.

In the present invention, the ELISA kit does not need to be particularly limited as long as it contains a PD-1 carrier and a detection marker as essential elements, and other reagents and the like as necessary.

One example is a 96-well microplate on which PD-1 protein is solid-phased as a PD-1 carrier, a combination of a biotin-labeled anti-PD-L1 antibody and a biotin quantification reagent as a detection marker, or the like.

As described above, the inventors have found that the PD-1 binding property of soluble PD-L1 mainly depends on sugar chain modification. As shown in the below-mentioned Examples, the sugar chain modification of PD-L1 varies widely, and the binding property to PD-1 also varies depending on the mode of sugar chain modification. On the basis of the findings, the present invention evaluates the binding characteristics to PD-1 by deglycosylating soluble PD-L1 in a sample of biological origin and analyzing the obtained pattern of deglycosylation of soluble PD-L1, based on which pathology, prognosis or treatment effect in a disease involving T cell immunity, diagnosis of applicability, treatment effect and side effect prediction of immunotherapy can be evaluated, or the evaluation can be assisted.

The deglycosylation pattern can be analyzed by, as shown in the below-mentioned Examples, glycosylating a sample of biological origin possibly containing soluble PD-L1 by treating with glycosidase (e.g., PNGaseF) or a sugar chain synthesis inhibitor (e.g., tunicamycin), and examining changes in the molecular weight by Western blot using the sample after treatment and an anti-PD-L1 antibody.

EXAMPLE

While the present invention is described in detail using Experimental Examples, these do not limit the scope of the present invention. The reagents and materials to be used are commercially available unless otherwise specified.

<<Outline of Experiment Method>>

1. Patient Sample

In the experiments, blood samples collected from patients with non-small cell lung cancer after approval from the Ethics Committee of Medical Research of the university (University of Occupational and Environmental Health, Japan) were used.

2. DNA Construct

Human PD-1-Ig expression vector and Human PD-L1 and PD-L2 expression vector were produced by inserting cDNA fragments into pEF BOS vectors.

3. Cell Line

PD-L1 and PD-L2 expressing 293T cell lines were produced by introducing human PD-L1 and PD-L2 expression vectors into 293T cells (293 cells introduced with SV40T (human embryonic kidney epithelial cell)) by the use of Gene Jammer. PC9 cells (derived from human lung adenocarcinoma) and REAF-LC-A1 cells (derived from human lung squamous cell carcinoma) were cultured in RPMI complete medium.

4. Purification of PD-1-Ig Protein

Human PD-1-Ig expression vector was introduced into 293T cells by the calcium phosphate method. Seven days later, the culture supernatant was recovered, and Human PD-1-Ig protein was purified by affinity chromatography using Protein G.

5. Deglycosylation

Blood samples were deglycosylated by PNGaseF treatment and cells were deglycosylated by treating with tunicamycin. Each sample before and after the treatment was analyzed by Western blot.

6. FACS Analysis

For FACS analysis, the cells to be used in the Experimental Examples were reacted with primary antibody or PD-1-Ig protein, and secondary labeled antibody in this order, and analyzed using FACS Calibur (manufactured by BD Biosciences).

7. Development of New ELISA System

Two kinds of ELISA plates coated with an anti-PD-L1 antibody and a PD-1-Ig protein were produced, a recombinant PD-L1 protein (R&D) with a known concentration was added, and colorimetric quantification was performed by immunoassay using a biotin-labeled anti-PD-L1 antibody.

A concentration-dependent increase in the absorbance was found within the range of 156-10000 pg/mL PD-L1 protein in ELISA coated with an anti-PD-L1 antibody, and within the range of 316-200000 pg/mL in ELISA coated with a PD-1-Ig protein. From the two analytical curves, the amount of bsPD-L1 in the total PD-L1 protein was determined and used as the standard value in the following experiments.

Experimental Example 1. Confirmation of Binding Property of PD-1-Ig Protein and PD-1 Ligand 1. An experiment was performed to confirm whether the produced human PD-1-Ig binds to a PD-1 ligand.
2. FACS analysis of 293T cells expressing PD-L1 and PD-L2, which are physiological ligands of PD1, was performed by reacting with PD-1-Ig protein, biotin-labeled anti-human IgG antibody, and APC-labeled streptavidin in this order. The expressions of PD-L1 and PD-L2 were analyzed by FACS using an anti-human PD-L1 antibody and an anti-human PD-L2 antibody. As a control, the same analysis was performed with 293T cells before expressing PD-L1 and PD-L2.
3. The results are shown in FIG. 1.
(1) With the anti-human PD-L1 antibody, only PD-L1-expressing 293T cells were stained, and 293T cells and PD-L2-expressing 293T cells were not stained. Therefrom it was confirmed that PD-L1-expressing 293T cells were correctly produced.
(2) Similarly, with anti-human PD-L2 antibody, only PD-L2-expressing 293T cells were stained, and 293T cells and PD-L1-expressing 293T cells were not stained. Therefrom it was confirmed that PD-L2-expressing 293T cells were correctly produced.
(3) Furthermore, with PD-1-Ig, PD-L1-expressing 293T cells and PD-L2-expressing 293T cells were stained, but 293T cells were not stained. Therefrom it was confirmed that PD-1-Ig was specifically bound to PD-L1 and PD-L2.
4. From these results, it was confirmed that human PD-1-Ig produced in accordance with the outline of the above-mentioned experimental method was correctly produced and recognized PD-L1 and PD-L2 as ligands.

Figure 2:
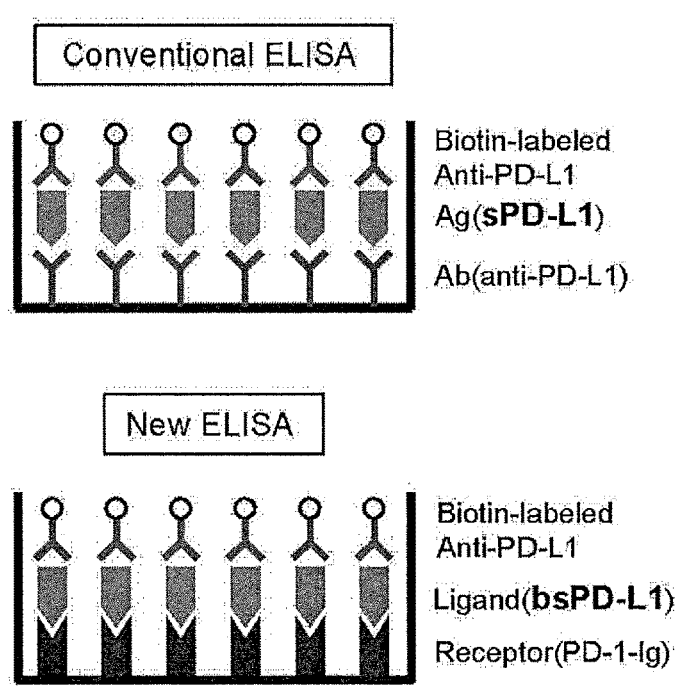
FIG. 2 schematically explains the ELISA of the present invention and conventional ELISA method.
Figure 3:
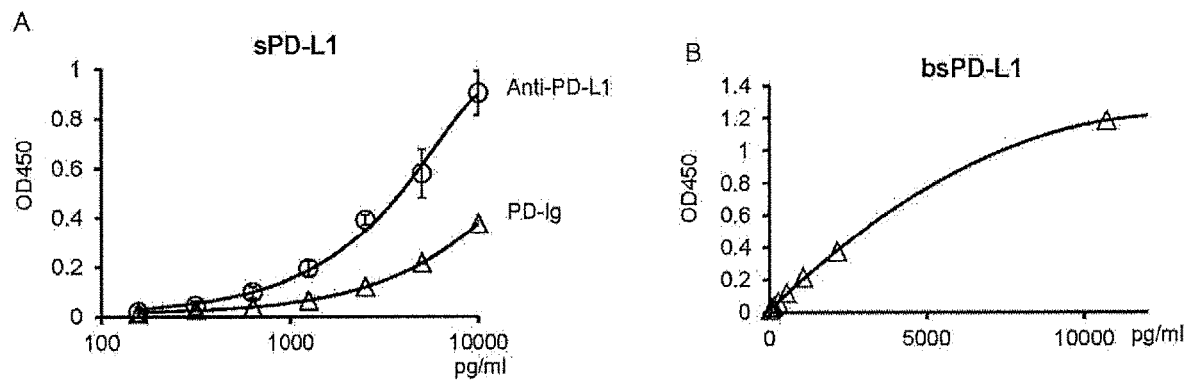
FIG. 3 shows (A) the results of measurement of sPD-L1 with a known concentration by using the present invention and the conventional method, and (B) the calculation results of bsPD-L1 amount based on the results (A).

Experimental Example 2. Development of New ELISA System for Detecting bsPD-L1 Based on PD-1 Binding 1. As a new system for detecting and quantifying PD-L1, an evaluation system (ELISA plate) using PD-1-Ig was produced (FIG. 2, example, New ELISA). As a control, an evaluation system using an anti-PD-L1 antibody was also produced by a similar method (FIG. 2, comparison example, Conventional ELISA).
2. ELISA plates were produced by respectively coating with anti-PD-L1 antibody and PD-1-Ig protein.
(1) An anti-PD-L1 antibody solution or a PD-1-Ig solution was added to a hydrophobic 96-well plastic plate, and the plates were sealed and allowed to stand.
(2) After removal of the supernatant and washing, a blocking solution was added and the mixture was allowed to stand.
(3) The blocking solution was removed and the plates washed with a washing solution were used as ELISA plates in the following studies.
3. To the produced ELISA plates was added a recombinant PD-L1 protein (R&D) with a known concentration, and colorimetric quantification was performed by immunoassay using a biotin-labeled anti-PD-L1 antibody.
4. The results are shown in FIG. 3.
(1) A concentration-dependent increase in the absorbance was found within the range of an addition concentration of 316-200000 pg/mL of recombinant PD-L1 protein in ELISA coated with PD-1-Ig protein (example) (FIG. 3A, mark—triangle).
(2) A concentration-dependent increase in the absorbance was found within the range of a concentration of 156-10000 pg/mL of recombinant PD-L1 protein in ELISA coated with anti-PD-L1 antibody (comparison example) (FIG. 3A, mark—circle).
5. From the two analytical curves, the amount of bsPD-L1 in the total PD-L1 protein was determined and used as the standard value in the following experiments (FIG. 3B).

Experimental Example 3. Study of Non-Small Cell Lung Cancer Patient Sample

Figure 4:
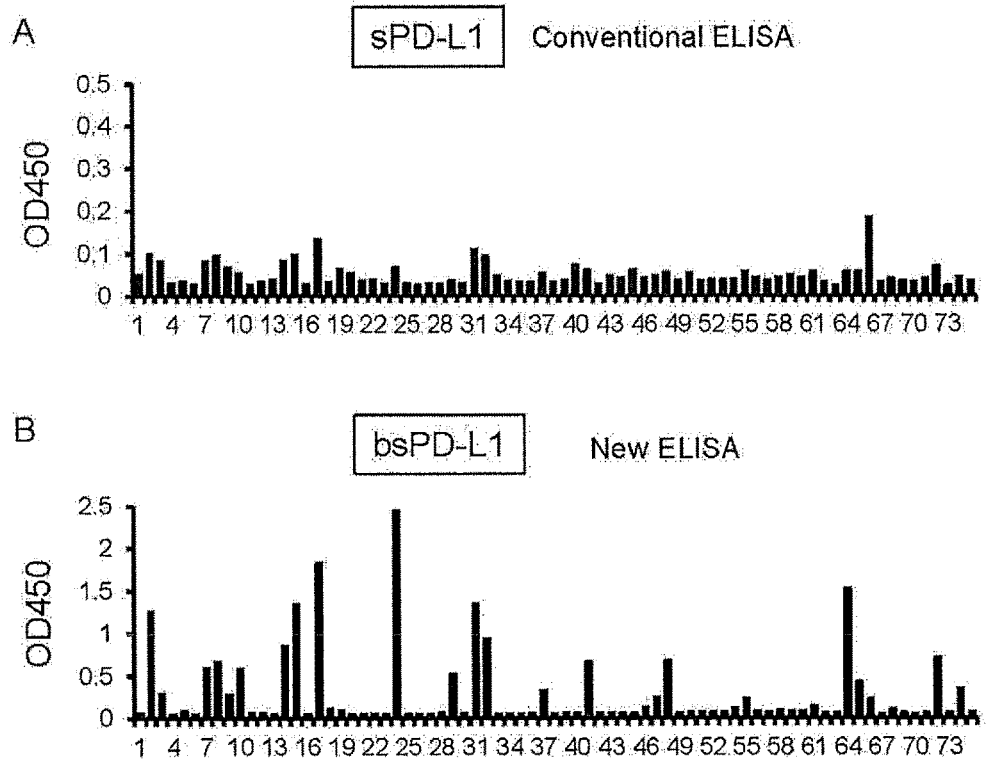
FIG. 4 shows detection and quantification results of sPD-L1 and bsPD-L1 in the plasma of non-small cell lung cancer patients by the use of the present invention and the conventional method.

1. About 70 plasma samples of non-small cell lung cancer patients were detected using respective ELISA plates of the example and comparison example, and the results were studied by comparison.
2. The results are shown in FIG. 4.
(1) In comparison example, the OD values were entirely low (0.05±0.03), and the detection rate was 2 out of 75 samples (2.7%) (FIG. 4A).
(2) On the other hand, in example, the OD values were entirely high (0.29±0.46) as compared to comparison example, and the detection rate was 26 out of 75 samples (34.7%), and the detection pattern thereof was markedly different.
3. From these results, it was considered that the example has higher detection sensitivity than the comparison example, and can detect sPD-L1 with high sensitivity that cannot be detected in the comparison example.

Experimental Example 4. Influence of Kind of Blood Sample and Anticoagulant

Figure 5:
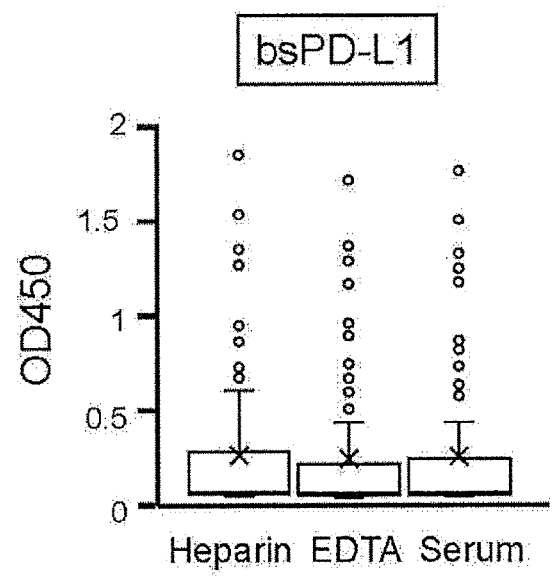
FIG. 5 shows the results of the comparison and study of the influence of an anticoagulator on the present invention and the conventional method.

1. In actual medical setting, sample collection and storage conditions are different. To find out the optimal conditions for clinical sample measurement, influence of the kind of blood sample and anticoagulant were investigated.
2. The results are shown in FIG. 5. The bsPD-L1 value (OD) of the detectable sample was higher in heparin plasma than in EDTA plasma or serum, thus suggesting higher stability.

Experimental Example 5. Influence of Sugar Chain Modification

Figure 6:
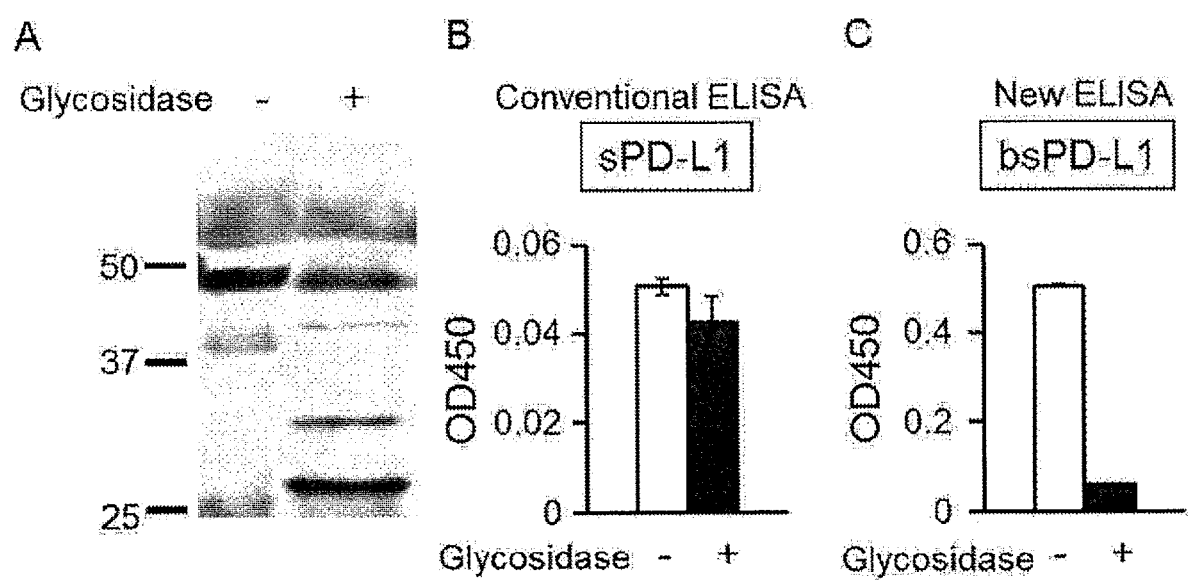
FIG. 6 shows an influence of a deglycosylation treatment of sPD-L1 and bsPD-L1 in patient samples in the present invention and the conventional method.
Figure 7:
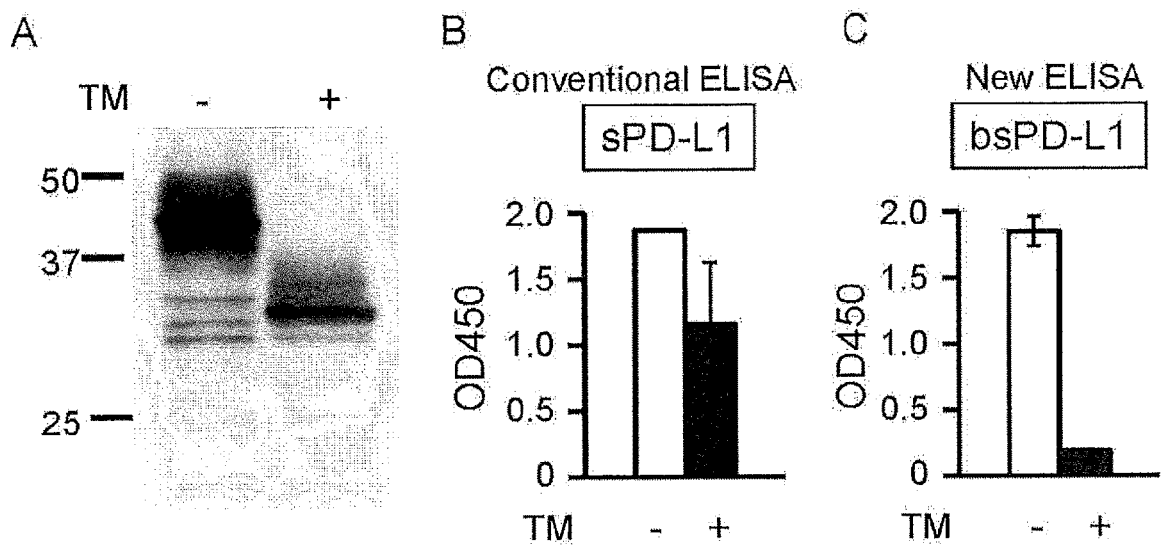
FIG. 7 shows influence of a deglycosylation treatment of sPD-L1 and bsPD-L1 in 293T cells in the present invention and the conventional method.
Figure 8:
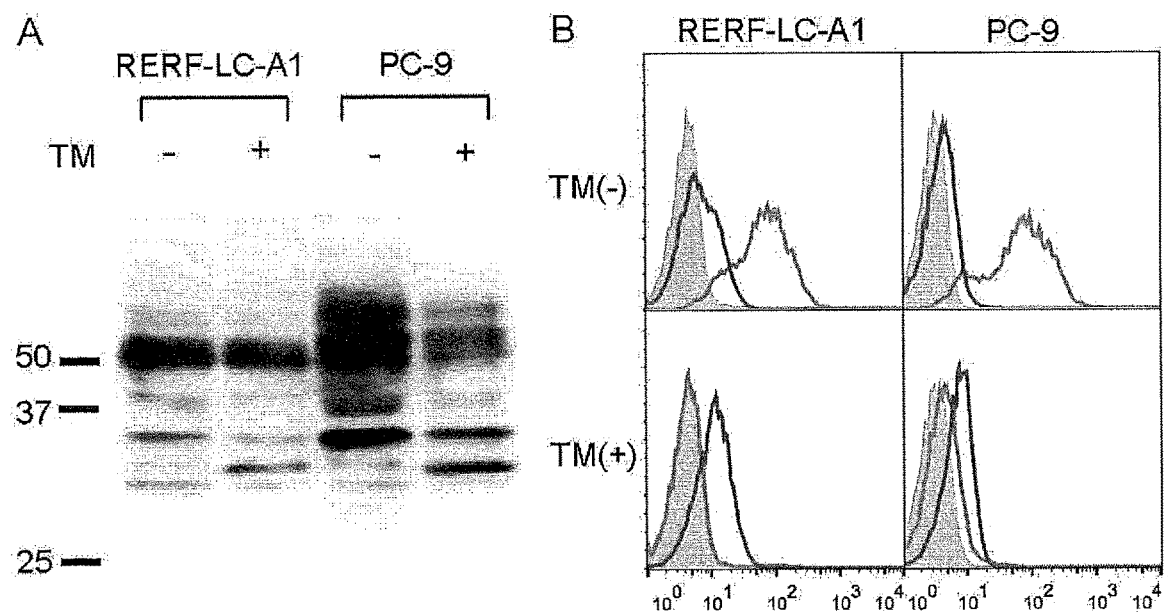
FIG. 8 shows influence of a deglycosylation treatment of sPD-L1 and bsPD-L1 in human squamous carcinoma cell or human lung adenocarcinoma cell in the present invention and the conventional method.

1. Since the detection sensitivity and the detection pattern are different between example and comparison example, it is possible that they detect sPD-L1s different in quality. As one of the possibilities, influence of sugar chain modification of sPD-L1 was examined.
2. A comparison of the detection results before and after the deglycosylation treatment in patient samples is shown in FIG. 6.
(1) A band of sPD-L1 in a patient sample is detected at about 45 kD when sugar chain modification exists. When deglycosylated by PNGaseF treatment, a band of about 25 kD is detected (FIG. 6A).
(2) When detection was performed on patient samples before and after the deglycosylation treatment by PNGaseF treatment, almost no change in the OD value was observed in comparison example (FIG. 6B).
(3) On the other hand, in example, the OD value markedly decreased by the deglycosylation treatment (FIG. 6C).
(4) From this, it was found that deglycosylation of soluble PD-L1 in patient blood greatly attenuated the binding to PD-1.
3. A comparison of detection results before and after deglycosylation treatment using 293T cells overexpressing membrane-type PD-L1 is shown in FIG. 7. pEF-BOS-neo/hPD-L1 was used for transfection.
(1) In 293T cells overexpressing membrane-type PD-L1, expression of sugar-chain-modified membrane-type PD-L1 is observed at around 55 kD. When deglycosylated by tunicamycin (TM) treatment, a band of about 33 kD is detected (FIG. 7A).
(2) When detection was performed on 293T cells before and after deglycosylation treatment by tunicamycin treatment, almost no change in the OD value was observed in comparison example (FIG. 7B).
(3) On the other hand, in example, the OD value markedly decreased by the deglycosylation treatment before and after the treatment (FIG. 7C).
(4) From this, it was found that deglycosylation of membrane-type PD-L1 in 293T cells greatly attenuated the binding ability to PD-1.
4. The results obtained by examining the sugar chain modification of membrane-type PD-L1 in a human lung cancer-derived cell line are shown in FIG. 8.
(1) Expression of sugar chain modified membrane-type PD-L1 is found at around 55 kD in human lung squamous cell carcinoma-derived RERF-LC-A1 cells and at around 65 kD in human lung adenocarcinoma-derived PC9 cells. When deglycosylated by tunicamycin treatment, a band of not more than 37 kD is detected (FIG. 8A).
(2) In RERF-LC-A1 cells, the binding property to PD-1-Ig was attenuated by the deglycosylation treatment (FIG. 8B).
(3) In PC9 cells, the binding property to PD-1-Ig was also attenuated by the deglycosylation treatment (FIG. 8B).
(4) Therefrom it was found that deglycosylation of human-derived PD-L1 expressed on the surface of a membrane greatly attenuates the binding ability to PD-1.
5. From these results, it was found that in example, glycosylated sPD-L1 was detected, but deglycosylated sPD-L1 was not detected or extremely weakly detected. In addition, the same also applies to membrane-type PD-L1.
6. On the other hand, in comparison example, sPD-L1 was detected regardless of the presence or absence of glycosylation, but it was found that the binding ability to PD-1 could not be evaluated. In addition, the same also applies to membrane-type PD-L1.
7. From the foregoing, it was found that glycosylated PD-L1 has a stronger binding ability to PD-1 than non-glycosylated PD-L1, and is detected with high sensitivity by the evaluation system of example based on PD-1 binding ability.

Experimental Example 6. Association with Prognosis of Lung Cancer

Figure 9:
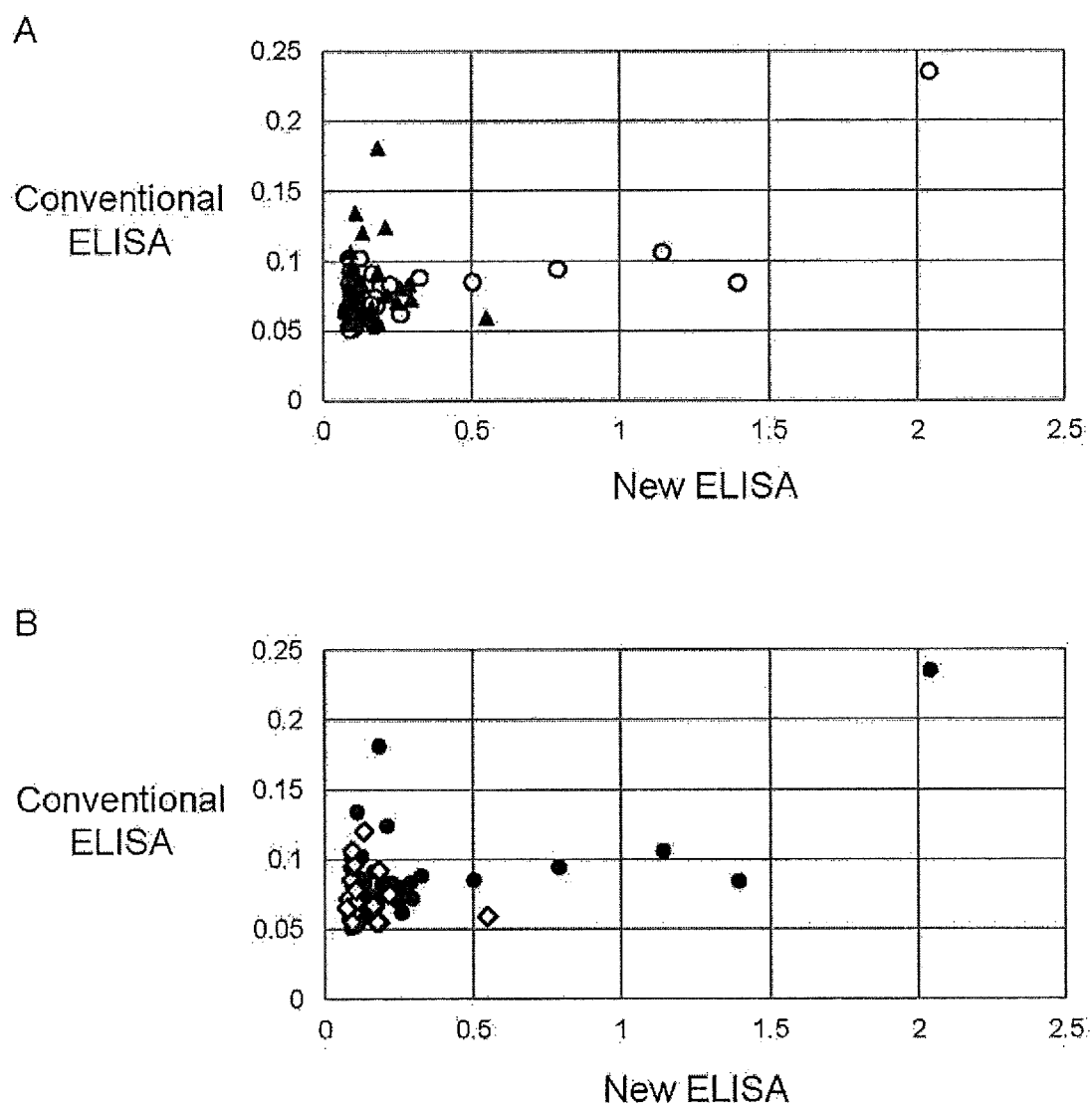
FIG. 9 shows comparison study of the prognosis of each patient in FIG. 4 with the results of the OD value by plotting them.

1. With regard to the patient samples measured in FIG. 4, FIG. 9 shows the results of the OD value of comparison example on the Y axis and the OD value of example on the X axis.
(1) In FIG. 9A, a patient group with a good prognosis without recurrence for not less than 2 years is shown in green (mark—open circle). This patient group with a good prognosis tended to show relatively high bsPD-L1.
(2) In FIG. 9B, a patient group with a poor prognosis who died due to recurrence is shown in red (mark—white rhombus). This patient group with a poor prognosis tended to show relatively low bsPD-L1.
2. These results indicate that the evaluation of bsPD-L1 according to example may be useful for predicting the prognosis of lung cancer.

Figure 10:
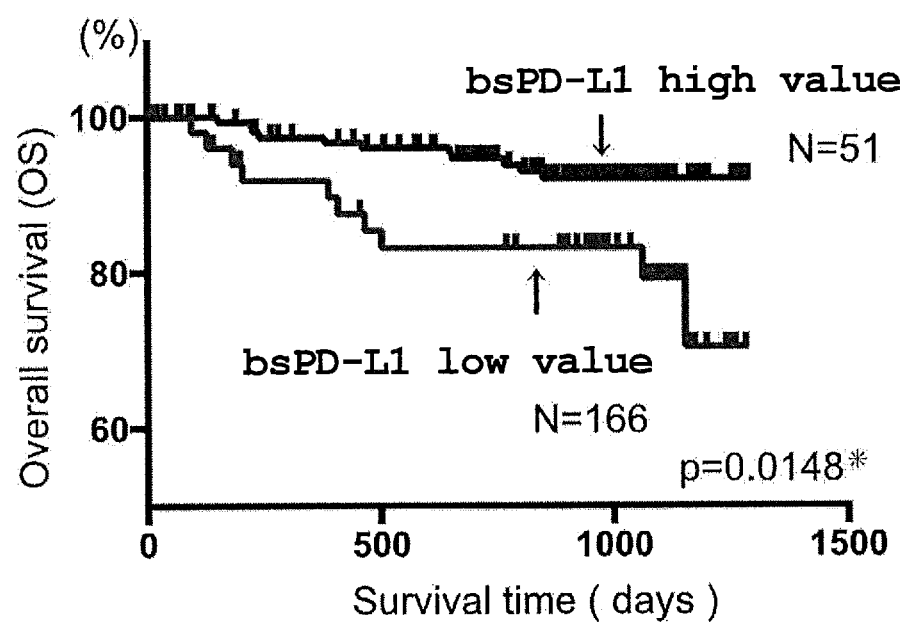
FIG. 10 shows survival curves indicating the relationship between the value of bsPD-L1 in the plasma of non-small cell lung cancer patients and the prognosis.

Experimental Example 7. Relationship Between Prognosis and bsPD-L1 in Plasma of Non-Small Cell Cancer Patients Sample: 217 preoperative plasma samples from patients diagnosed with non-small cell lung cancer and having undergone permanent cure surgery
Method: The above-mentioned samples were measured for bsPD-L1 value using new ELISA (example), and the relationship between preoperative bsPD-L1 value and overall survival (OS) was analyzed retrospectively. For the cutoff value, an ROC curve was created from the OS and the optimal value was determined (30 pg/ml).
Results: The results are shown in FIG. 10. The prognosis of the bsPD-L1 high group (n=51) was better than that of the bsPD-L1 low group (n=166).
In cancer patients, the result that the bsPD-L1 high group showed a good prognosis is contrary to the result predicted from the prior art, "the sPD-L1 high group has a poor prognosis", and it was found that selective detection and quantification of specific PD-L1 (bsPD-L1) having a binding ability to PD-1 among soluble PD-L1 (sPD-L1) is clinically significant.

INDUSTRIAL APPLICABILITY

According to the present invention, a new detection and quantification method for evaluating immunity of individual, particularly T cell immune function in clinical setting, a convenient novel ELISA system to be used for the evaluation, and a kit thereof are provided.
The evaluation method of the present invention is expected to be applicable to the diagnosis and evaluation of not only cancer which is a representative disease in which T cell immunity is involved in pathology, but also infectious disease, autoimmune disease, allergy, rejection in transplantation, lifestyle-related disease and the like.

The ELISA system of the present invention can conveniently evaluate immunity, particularly T cell immune function, of individuals, and is expected to provide pathology evaluation of various diseases involving T cell immune response, and diagnoses of prognosis of cancer, applicability of immunotherapy including immune checkpoint inhibitors and treatment effects.

This application is based on patent application No. 2017-172593 filed in Japan (filing date: Sep. 8, 2017), the contents of which are encompassed in full herein.

The invention claimed is:

1. A method for evaluating T cell immune function, comprising (a) a step of reacting a test sample and programmed cell death 1 (PD-1), (b) a step of detecting and quantifying a soluble programmed cell death 1-ligand 1 (PD-L1) bound to PD-1 as soluble PD-L1 with PD-1-binding capacity (bsPD-L1), wherein the bsPD-L1 is a sugar chain-modified PD-L1, and (c) a step of evaluating pathology, prognosis, or treatment effect in a disease involving T cell immunity or a step of evaluating diagnosis of applicability, treatment effect, and side effect prediction of immunotherapy.

2. The evaluation method according to claim 1, wherein the test sample is a sample of biological origin.

3. The evaluation method according to claim 1, further comprising a step of reacting an anti-PD-L1 antibody and the test sample, and detecting and quantifying soluble PD-L1 (sPD-L1) in the test sample, wherein the results are combined and evaluated.

4. The evaluation method according to claim 1, which comprises the step of evaluating pathology, prognosis, or treatment effect in a disease involving T cell immunity.

5. The evaluation method according to claim 4, wherein the disease involving T cell immunity is cancer.

6. The evaluation method according to claim 1, which comprises the step of evaluating diagnosis of applicability, treatment effect, and side effect prediction of immunotherapy.

7. The evaluation method according to claim 5, wherein a good prognosis can be predicted when the amount or concentration of bsPD-L1 in the test sample is not less than the cutoff value.

* * * * *